United States Patent [19]

Avitall

[11] Patent Number: 5,327,905
[45] Date of Patent: Jul. 12, 1994

[54] BIPLANAR DEFLECTABLE CATHETER FOR ARRHYTHMOGENIC TISSUE ABLATION

[76] Inventor: Boaz Avitall, 4868 N. Ardmore Ave., Milwaukee, Wis. 53217

[21] Appl. No.: 989,804

[22] Filed: Dec. 11, 1992

Related U.S. Application Data

[63] Continuation-in-part of Ser. No. 909,867, Jul. 7, 1992, which is a continuation-in-part of Ser. No. 835,553, Feb. 14, 1992, abandoned.

[51] Int. Cl.⁵ ................................................ H61B 5/00
[52] U.S. Cl. ..................................... 128/772; 128/642; 606/45; 607/122
[58] Field of Search ............... 128/656, 657, 658, 772, 128/639, 642, 784, 785, 786, 790; 606/45, 46, 47, 48, 49; 604/53, 280, 281, 282; 607/115, 119, 122, 72

[56] References Cited

U.S. PATENT DOCUMENTS

| | | | |
|---|---|---|---|
| 4,273,111 | 6/1981 | Tsukaya | 128/772 |
| 4,522,212 | 6/1985 | Gelinas et al. | 128/786 X |
| 4,586,923 | 5/1986 | Gould et al. | 128/657 X |
| 4,619,263 | 10/1986 | Frisbie et al. | 128/772 X |
| 4,638,802 | 1/1987 | Okada | 606/47 |
| 4,641,649 | 2/1987 | Walinsky et al. | |
| 4,660,571 | 4/1987 | Hess et al. | |
| 4,664,113 | 5/1987 | Frisbie et al. | 128/657 X |
| 4,677,990 | 7/1987 | Neubauer | 128/786 |
| 4,682,596 | 7/1987 | Bales et al. | |
| 4,699,147 | 10/1987 | Chilson et al. | 128/642 |
| 4,777,955 | 10/1988 | Brayton et al. | 128/642 |
| 4,785,815 | 11/1988 | Cohen | |
| 4,869,248 | 9/1989 | Narula | 128/784 |
| 4,882,777 | 11/1989 | Narula | 128/786 X |
| 4,920,980 | 5/1990 | Jackowski | 128/786 |
| 4,922,912 | 5/1990 | Watanabe | 128/786 X |
| 4,960,134 | 10/1990 | Webster, Jr. | 128/786 |
| 5,055,109 | 10/1991 | Gould et al. | 128/657 X |
| 5,056,526 | 10/1991 | Khalil | 607/122 X |
| 5,078,717 | 1/1992 | Parins et al. | 606/48 |
| 5,117,828 | 6/1992 | Metzger et al. | 128/784 |
| 5,117,839 | 2/1992 | Dance | 128/657 X |
| 5,185,004 | 2/1993 | Lashinski | 604/280 X |

*Primary Examiner*—Lee S. Cohen
*Assistant Examiner*—Samuel Gilbert
*Attorney, Agent, or Firm*—Haugen and Nikolai

[57] ABSTRACT

A vascular catheter has a highly flexible distal section. A biplanar control system is provided for enabling and controlling the movement of the distal catheter section and tip in any direction in a manner such that the distal tip is capable of accessing any point on the wall of the chamber entered. Dual-wire biplanar control system embodiments include a vertical deflection control wire operable to deflect the distal tip of the catheter in a controlled manner in a vertical plane substantially parallel to the longitudinal axis of the tubular catheter and a lateral deflection control wire operable to deflect the distal tip of the catheter in a controlled manner in a lateral plane substantially perpendicular to the longitudinal axis of the tubular catheter. A one-wire system for both vertical and lateral control is also described.

32 Claims, 7 Drawing Sheets

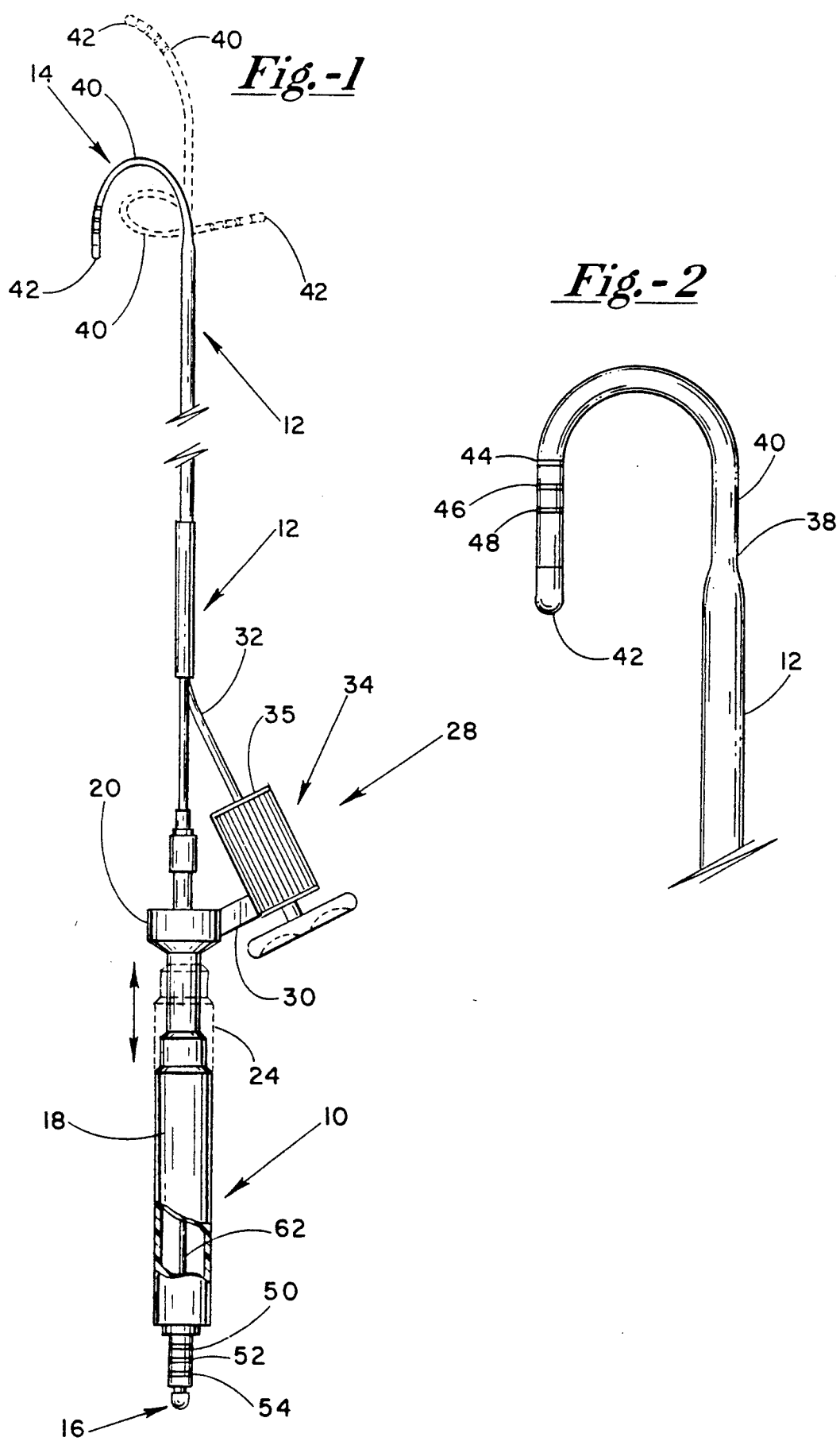

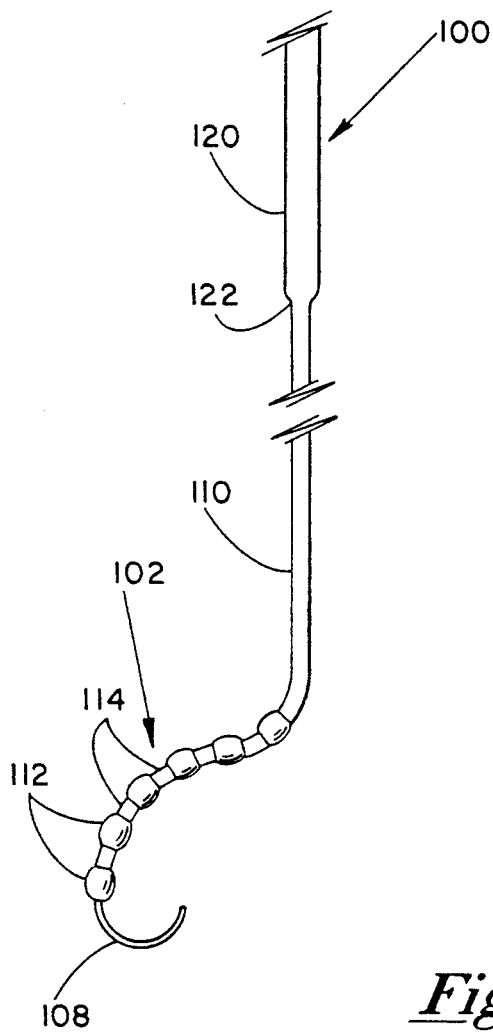
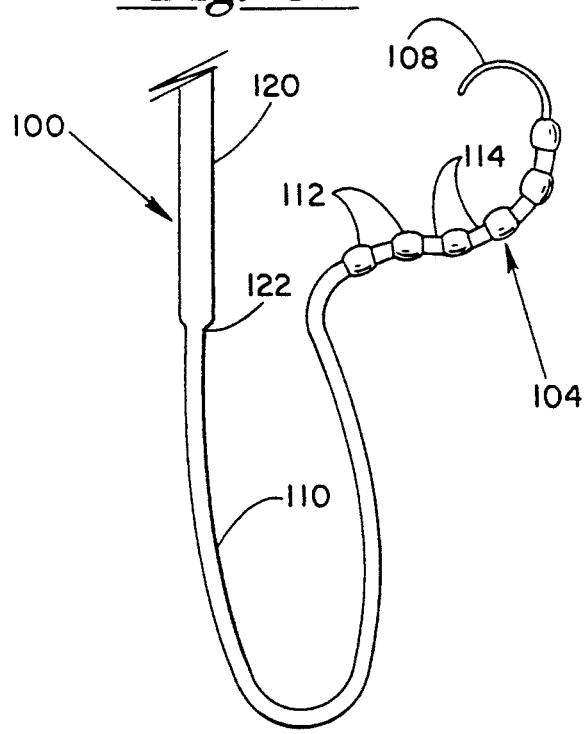
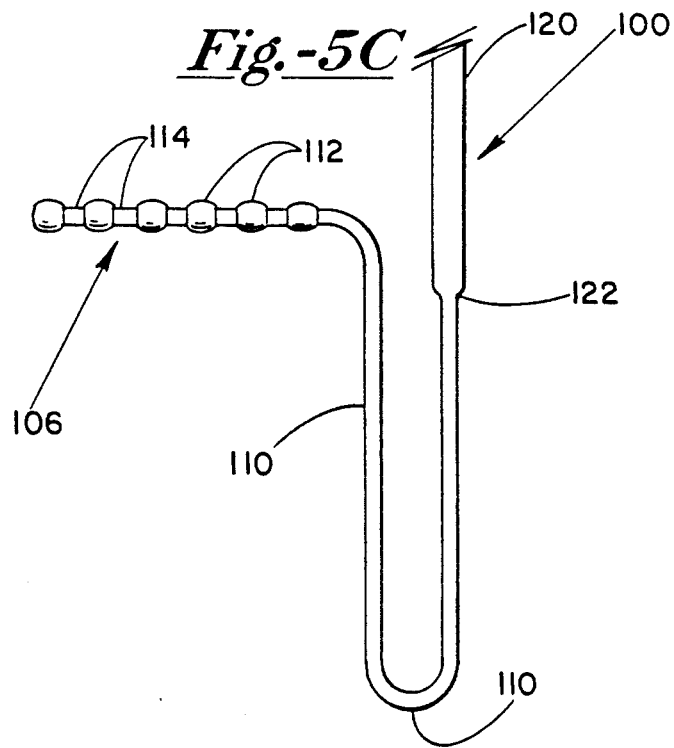

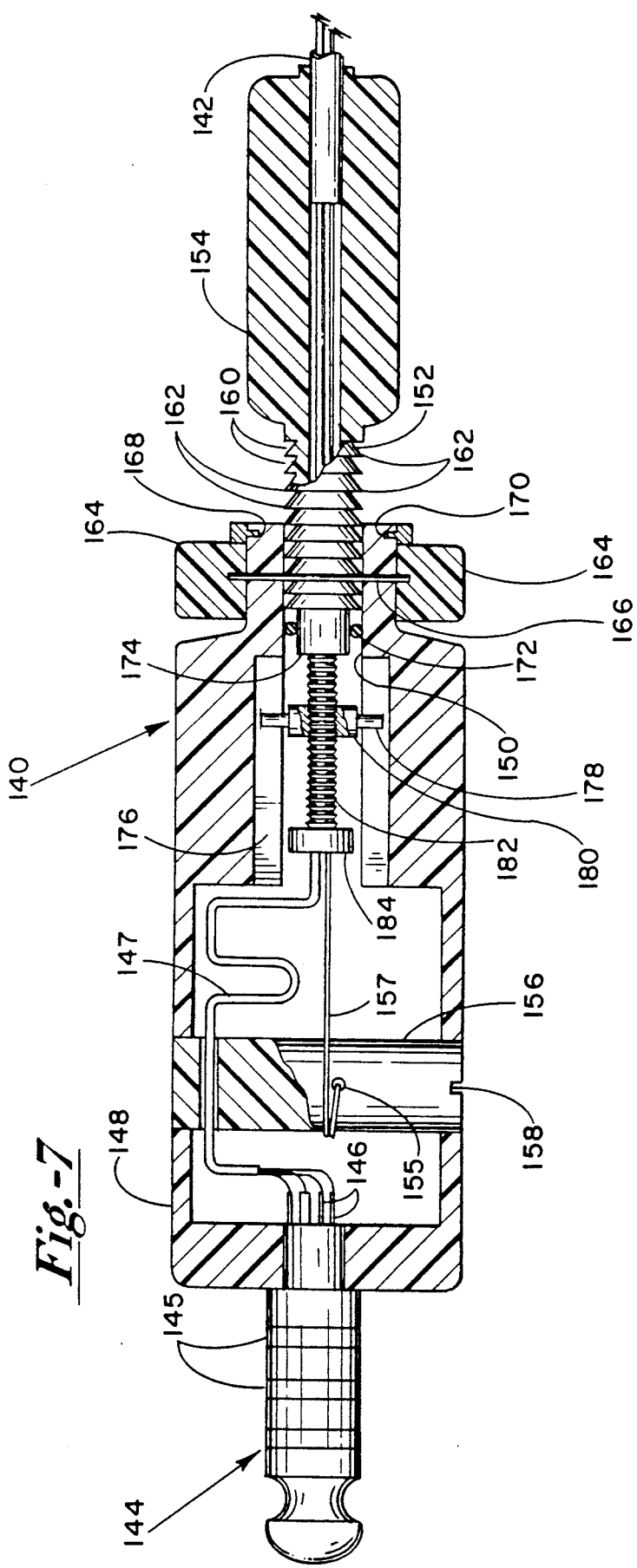

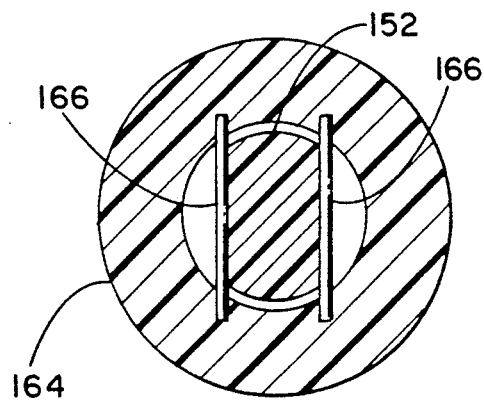
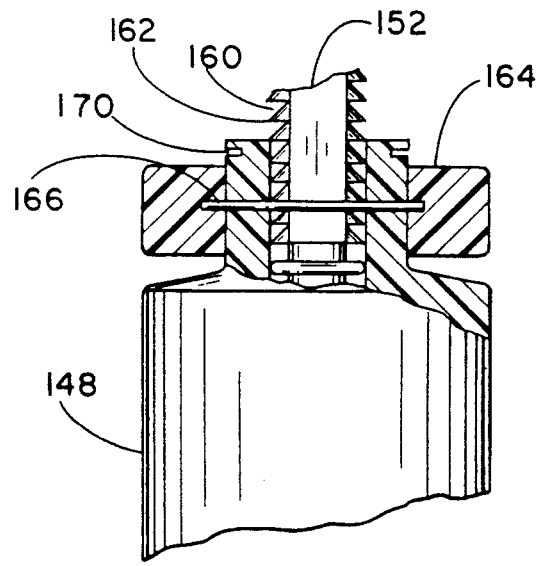
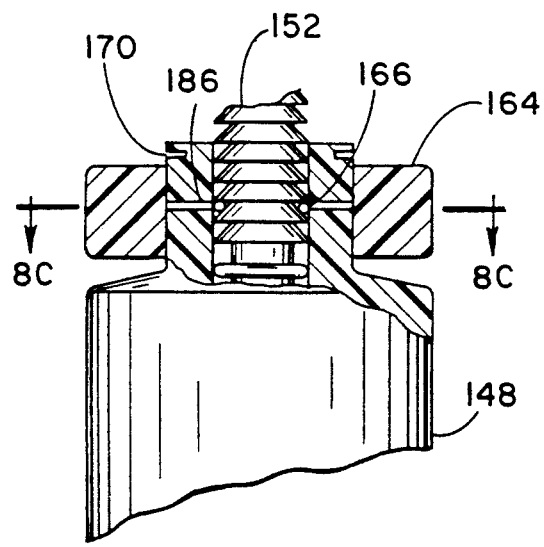

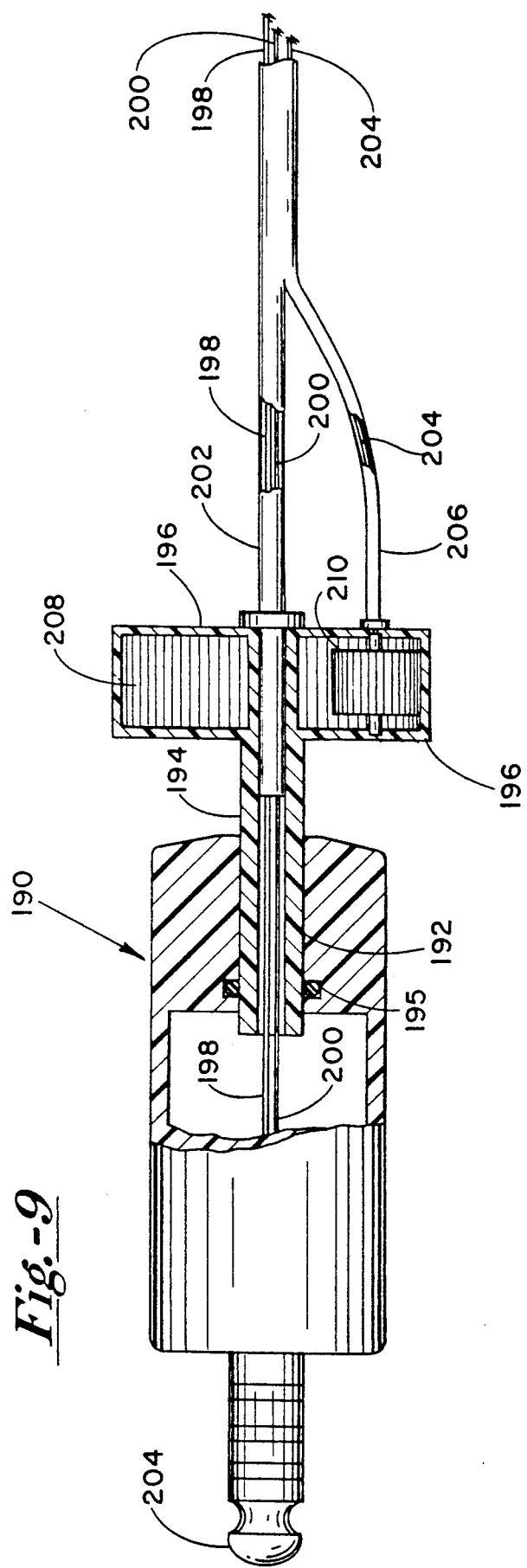

BIPLANAR DEFLECTABLE CATHETER FOR ARRHYTHMOGENIC TISSUE ABLATION

BACKGROUND OF THE INVENTION

Cross-Reference to Related Application

This patent application is a continuation-in-part of co-pending application Ser. No. 07/909,867, filed Jul. 7, 1992, which, in turn, is a continuation-in-part of application Ser. No. 07/835,553, filed Feb. 14, 1992, now abandoned.

Reference is made to applications Ser. Nos. 07/840,026 and 07/909,869, which is a continuation-in-part of application Ser. No. 07/840,162 of common inventorship. Each of the cross-referenced applications also are directed to improved catheters.

Field of the Invention

The present invention is directed generally to an improved catheter apparatus for use in the field of cardiac arrhythmia ablation. In particular, the invention involves the use of a biplanar deflection system which greatly increases the maneuverability of the catheter tip in the lateral plane generally perpendicular to that of the disposition of the main catheter tube. This allows the operator to direct the tip of the catheter in multiple directions and maneuver the catheter as close as possible to the site of the arrhythmogenic tissue of interest to accomplish effective ablation.

Discussion of the Related Art

Normal cardiac pacing, in a healthy heart, is controlled by a special structure known as the sinoatrial node (SA node). This is the natural pacemaker of the heart and is a specialized tissue located within the muscle walls of the right atrium. The SA node provides impulses which dominate the inherent or natural rhythmic contractions of the heart atria and the ventricles. This dominance or control involves the transmission of ionic impulses through cardiac conduction pathways in the atria and the ventricles which cause the heart to contract and relax in an orderly sequence at a rate dictated by the SA node. This sequence ensures that blood flow to the systemic circulation or the pulmonary system will be maximized with each ventricular contraction. The SA node has its own inherent rate which can be modified by signals from the nervous system. In response to excitement, physical activity, etc., the sympathetic and parasympathetic nervous systems react to modify the rate.

A depolarization impulse begins with the SA node and spreads as an electrical wave from its location in the right atrium across to the left atrium and down toward the transition zone between the atrium and the ventricles where another node, known as the atrioventricular (A-V) node or junction, is located. This impulse conducts through the A-V node in a slower fashion and continues to a common pathway known as the Bundle of His between the right and left ventricles, then into multiple paths called right and left bundle branches, each bundle branch supplying one ventricle. These bundle branches then divide into an extensive network of finer paths of conducting tissue which spread from the inner to the outer surfaces of the heart and which are referred to as the Purkinje fibers. These fibers feed the depolarization impulse into all portions of the ventricular myocardium.

As long as this system is intact, impulses are transmitted normally and cardiac rhythm is maintained. The natural impulse or current flow in the cardiac conduction system, however, may be interrupted or altered by congenital defect, disease or injury which can cause the formation of scar tissue. When a sufficiently severe injury or a congenital defect is present in the cardiac conductive pathways or in the ventricular myocardium, the electrical impulses are not transmitted normally and rhythmic disturbances known as cardiac arrhythmias can occur. With respect to such disturbances, the term bradycardia is used to describe an abnormal slowing of the cardiac contractions and the term tachycardia is used to describe abnormally rapid heart action. While either of these conditions can endanger the life of the patient, tachycardia is more serious, particularly in patients having underlying heart disease.

Ventricular tachycardia and other ventricular arrhythmias have been treated with a number of drugs such as lidocaine, quinidine and procainamide. In cases of excessive sympathetic nervous activity or adrenal secretion, Beta blocking drugs have been used. In cases where drug therapy has been ineffective in preventing tachyarrhythmias, certain surgical procedures have been used to ablate the arrhythmogenic tissue either from the atrium or the ventricles. This procedure involves extensive surgery in which an incision through the pericardium and heart muscle is made to locate the arrhythmogenic tissue, which is then frozen or surgically removed to be replaced by scar tissue.

Because open-heart surgery is a high risk procedure which requires a prolonged period of hospitalization and recuperation, a less traumatic solution is needed. In response, catheters of various types have been devised and used for diagnosing and treating a number of cardiac abnormalities to avoid the trauma of open-heart surgery. For example, as a method for resolving atherosclerotic plaque build up, stenotic lesions are now routinely opened by the use of balloon angioplasty. In this procedure, a balloon carrying catheter is navigated through the patient's vascular system to the location of the stenosis. The balloon is inflated by fluid injected through a lumen of the catheter to apply pressure to the walls of the clogged vessel, thereby opening it.

Catheter devices have also been used to locate and ablate cardiac conduction pathways. One such device is shown in U.S. Pat. No. 4,785,815, in which a catheter tube carries at its distal end at least one electrode for sensing membrane potentials within the heart, together with a heating device for ablating at least a portion of the pathway located by the sensing device. Another thermal ablation catheter for microtransection or macrotransection of conduction pathways within the heart, which uses a resistive heating element at its distal end for highly localized treatment, is illustrated and described in U.S. Pat. No. 4,869,248. These devices are generally effective once the ablating element is properly positioned at the localized area of interest. A catheter device tip of the class described has also been developed which employs a single, handle-operated deflection wire. Such a device is disclosed in U.S. Pat. No. 4,960,134.

Electrophysiological catheter ablation procedures often have been hampered by the inability of the operator to maneuver the catheter tip to the precise location of the arrhythmogenic tissue. This is primarily a result of the limited maneuverability of the catheter tube itself. The catheter tube must have sufficient strength and stiffness to be guided through the vascular system to the vicinity of the tissue of interest. This construction does not allow the degree of flexibility at the tip of the catheter needed to perform intricate multidirectional manipulations in the highly localized areas involved. Available catheters, even catheters with single deflection wire control, are characterized by inadequate control of fine movements and have tips that can be deflected only in planes parallel to the main catheter tube. They lack the ability for controlled lateral movement in planes perpendicular to that of the main catheter tube within the atria or the ventricles.

Most present cardiac tissue ablation procedures involve the use of radio frequency (RF) electrical current transmitted to the tissue via a catheter which is positioned as closely as possible to the arrhythmogenic site within the atria or ventricles. Radio frequency electrical current heats the tissue surrounding the catheter, creating a discrete dense lesion. In order for the patient to be cured of the arrhythmia, the lesion must be created in the area from which the arrhythmia originates. Improvement in the maneuverability of such devices could optimize precise positioning of the catheter prior to ablation.

SUMMARY OF THE INVENTION

The present invention provides a new catheter design which endows the catheter tip with increased flexibility. The increased flexibility involves the incorporation of a biplanar deflection system which allows control of the lateral movements of the catheter tip.

The catheter system of the present invention includes an elongated flexible tubular catheter having a proximal end, a distal end and a central lumen extending therebetween. The outside diameter of the tubular catheter is such that it can be routed through the vascular system of a patient and into the heart chamber of interest to be treated. This is typically 7-8 French in size. The distal portion of the main tubular section of the catheter in the present invention includes a flexible distal tip section fabricated from a highly flexible reinforced polymer tubing material, preferably polyethylene, which is connected to the main catheter tube. A portion of this flexible tubing extends inside the distal end of the main tubing section of the catheter.

The flexible distal tip section of one embodiment includes a cylindrical metallic tip electrode which is preferably of noble metal such as platinum and, in one successful embodiment, is 4 mm long and 3 mm in diameter. One or more additional electrodes, preferably 2 or 3 ring electrodes, are serially spaced proximally from the tip electrode, typically starting 2 mm behind the tip electrode and spaced about 2 mm apart.

In an alternate embodiment, the electrode-carrying catheter tip section may have a "memory" in terms of a predetermined fixed shape which is re-assumed outside the conveying catheter lumen. This may be accomplished by using a flexible but memoried material which may be a plastic or a metallic material such as a nickel titanium alloy known commonly as nitinol. In this manner, specialized shapes to access and address specific internal cardiac areas may be created in mapping/ablation electrode tips which assume custom designed shapes when deployed. The mapping/ablation tips generally employ a plurality of serially spaced, separately connected electrodes in any desired configuration or number. The electrodes are typically up to 4 mm in length with 3 mm separations. The pre-shaped tips may be designed or readily adapted to operate with the tip deflection system of the invention, keeping in mind limitations of a fixed shape.

All of the electrodes are individually connected to an input/output device, typically an electrical phono jack type connector, by thin low resistance wire conductors. The phono jack or other connector is attached to the handle. The electrodes can be connected to a recording system which measures and displays cardiac depolarization potentials sensed within the involved cardiac chamber. This system can be used to map the earliest activation time indicating the most desirable location for tissue ablation. The tip electrode (or any other electrode) can be used for both electrical mapping when connected to the recording equipment and to deliver the ablation energy when connected to an energy source.

The system, in one embodiment, also includes a pair of control wires, a vertical deflection control wire and a lateral deflection control wire. The vertical deflection wire controls the deflection of the tip in a plane parallel to the main catheter tube (vertical deflection). It includes a wire, preferably of stainless steel, connected to a T-shaped pin, also preferably of stainless steel. The T-shaped pin is anchored or imbedded in the flexible distal section spaced about 3–4 mm from the tip electrode and provides the anchor for the vertical deflection wire.

The deflection of the tip is achieved by operating a longitudinally movable portion provided in the handle section which causes the wire to tense and relax. Tension in the vertical deflection wire inherently causes the tip to deflect since the insertion position of this wire is off center and in the side of the flexible portion of the catheter. This wire is threaded in the central lumen through the main body of the catheter to the handle.

Lateral deflection and control is achieved using highly torqueable wire which is flexible only at the end and which is inserted into the flexible deflectable distal portion of the catheter. The proximal portion of this wire is significantly more rigid. It is threaded through the length of the rigid portion of the catheter and extends out of the catheter tubing through a radial opening at a point spaced distally from the handle and is connected to a hand-operated rotatable lateral adjustment control knob mounted from the catheter handle at a fixed distance therefrom. The distal end of this wire is fixed to, usually by soldering, the tip electrode. Rotation of the knob left or right transmits rotational torque to the catheter tip. When the distal catheter tip is vertically deflected, the application of torque through this wire causes the distal tip to deflect laterally. The knob system is configured so that the knob can rotate freely when it is pushed down and locks in position when released. The rotational knob system is further designed to allow only a predetermined, limited number of rotations, possibly 5 or 6, to each side to prevent the operator from over-rotating the wire which could result in a fracture thereof.

Vertical deflection of the catheter tube is accomplished by longitudinal movement of the handle. Lateral movement control is achieved by turning the rotation knob in the desired direction. Adjustment of the rotation knob and the handle allow precise positioning of the tip in the heart.

Continuous recording of electrical activity while the catheter tip is in any deflection or rotational position is possible since the tip electrode is connected to a conductive wire which is connected to the phono connector. The tip is further connected to a source of radio frequency (RF) electrical current for ablation.

Alternate two-wire control systems and a further embodiment that utilizes a single wire to deflect the catheter both in the vertical direction and the horizontal direction by employing a highly torqueable material which can be both subject to tension and simultaneous rotation are illustrated.

BRIEF DESCRIPTION OF THE DRAWINGS

In the drawings, wherein like numerals are utilized to designate like parts:

FIG. 1 is a side view of the catheter system showing the flexible tip segment in various positions;

FIG. 2 is an enlarged fragmentary view depicting the flexible tip section of FIG. 1;

FIGS. 5A-5C show other embodiments of an electrode catheter tip of predetermined shape for the catheter system of the invention;

FIG. 7 is a fragmentary side view, partially in section, depicting an embodiment using a single control wire;

FIGS. 8A-8C are fragmentary rotated side views and a top view of details of the piston locking system for the handle of FIG. 7; and FIG. 9 is a fragmentary side view, partially in section, with parts broken away, of another alternate two-wire control handle embodiment of the invention.

DETAILED DESCRIPTION

Figure 3:
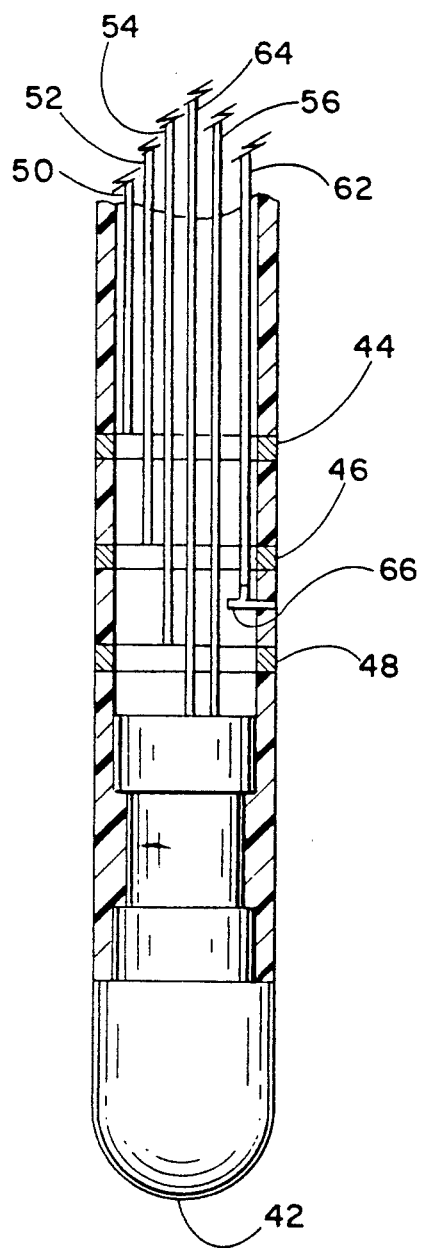
FIG. 3 is a further enlarged fragmentary view, with parts cut away, of the tip section of the catheter.

The biplanar tissue ablation catheter system is shown in FIG. 1 and includes a handle portion shown generally at 10, a central, relatively rigid tubular section 12, and a flexible distal maneuverable tip section 14. The central section 12 is shown broken as it depicts the long main body of the catheter.

The handle portion further includes an electrical jack-type plug-in device 16 having multiple input/output pick off points associated with conductors discussed below. An outer hand grip section 18 in the handle portion is made freely adjustable for a distance along the longitudinal axis of the handle relative to the inner tubular handle section 20. The distance of adjustment is further illustrated in phantom at 24. The handle includes a hand-operated rotatable lateral tip deflection control knob shown generally at 28, is fixed in position spaced from the handle by a mounting member 30 and connected with the central tubular section by a tubular member 32. The knob itself 34 is longitudinally and rotationally adjustable and will be more fully described in conjunction with FIG. 4, below. Relatively small tubular members 32 are threaded through the main catheter tube 12 which, in turn, is connected with the slightly necked-down flexible, maneuverable distal tip section 14 by a transition 38. The flexible tip section further includes a proximal segment of flexible reinforced polymer catheter tubing 40 which connects the distal end of the main catheter tube 12 and an electrode-containing platinum catheter tip system 42. The tubing segment 40 may be of any convenient length, typically about 4 to 8 centimeters, depending on the desired use.

The tubing segment may be of any biologically compatible, relatively inert polymeric material having the requisite strength and flexibility together with the ability to be incorporated with other catheter materials may be reinforced with materials to achieve needed characteristics. The thin, relatively flexible reinforced tubing generally has an ID of about 3 mm or less.

As shown, enlarged for greater clarity in FIGS. 2 and 3, the catheter tip system 42 includes a plurality of electrodes 44, 46 and 48 which are in electrical communication with the external environment of the tip and with respective insulated electrical conductors 50, 52 and 54. The conductors are threaded through the catheter tubes 40 and 12 and the handle to separate pick-offs on the jack 16. The ablation electrode 42 may be adapted to be connected as input to a recording system in a mapping mode or as output from a source of high frequency electrical power via conductor or conductors 56, when operated in an ablating mode, as desired.

The lateral tip deflection is achieved by high torque wire 64 which is connected to the tip electrode at the distal end and threaded through the central core of the catheter tubing and proximally through the tubing 32 to the lateral control knob 28. A vertical tip deflection control wire 62 is inserted into the deflectable portion of the catheter in an off-center position and has a distal extremity anchored to the catheter side wall by a T-shaped stainless steel pin 66 just below the tip electrode. The vertical deflection control wire 62 is threaded through the central lumen of the catheter to the handle 10 and the proximal end anchored to the movable portion of the handle 18. Sliding the handle member 18 on the shaft portion thereby results in vertical deflection changes of the flexible catheter tip.

Figure 4:
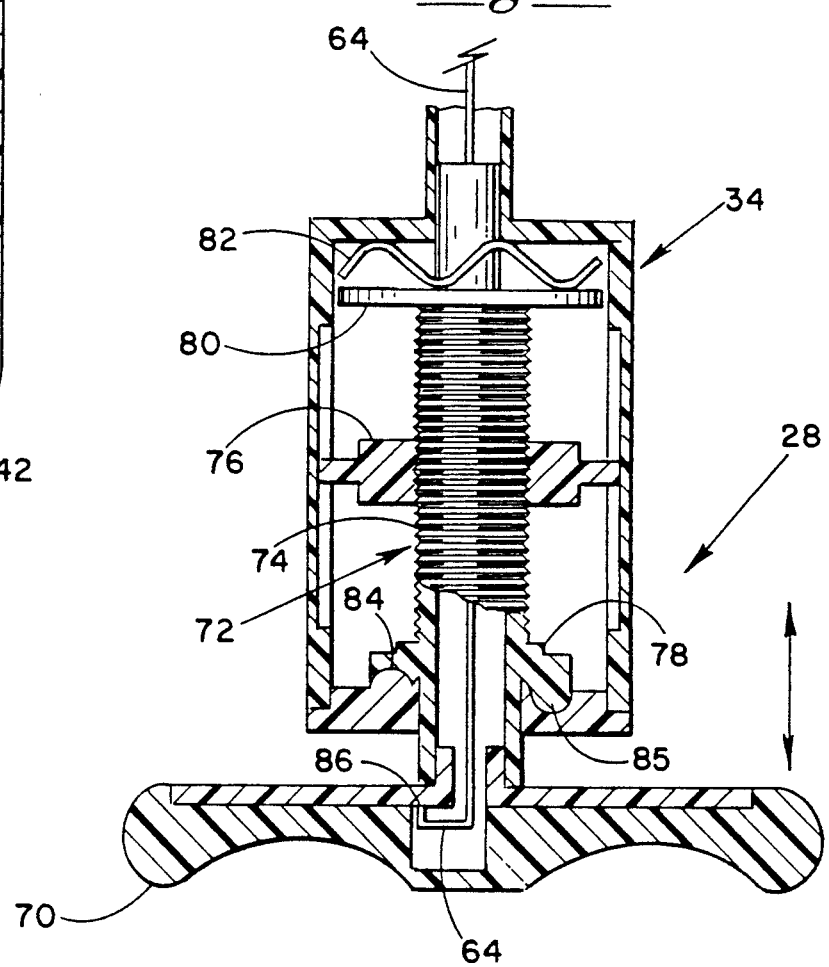
FIG. 4 is an enlarged view, partially in section, of the hand-operated, lateral tip deflection control knob.

The hand-operated rotatable lateral tip deflection control knob system is more fully described in relation to the enlarged view of FIG. 4. The hand-operated knob system 28 includes an outer cylindrical member 34, a finger-operated bidirectional adjustable knob member 70, connected to an internal cylinder 72 having a series of threads 74 and a rotating ring with threads 76. The ring 76 rides the main shaft and it is limited in the number of rotations by the lower shoulder 78 and upper limit stopper 80. A spring 82 pushes the knob member upward with respect to the handle 70 engaging the locking spline at 84 and 85. The control wire 64 traverses the knob system and is anchored on the knob at 86 so that the rotational torque applied to the control wire 64 is directly controlled by the rotation of the knob 70.

While it will be appreciated that any mechanical equivalent set-up can be used which accomplishes the aims of the hand-operated rotatable knob control system 28, the one pictured in FIG. 4 operates basically in the following manner. The knob 70, together with the attached internal cylinder 72, is reciprocally adjustable in the longitudinal direction against the return spring 82 such that when the handle 70 is pushed in, the rounds and sockets 84 and 85 disengage, allowing the threaded rod or cylinder 72 to be rotated with respect to the member 76. The end of the wire 64 is fixed in position in the knob 70 at 86 such that rotation of the knob 70 applies a rotational torque in the desired direction to the control wire 64, which is, in turn, transmitted to the tip 42. The spring 82 normally maintains the rounds and sockets in a meshed position such that relative rotation is otherwise precluded thereby maintaining the rotational torque on the wire 64 constant. The rotation of the knob 70 is limited by stops 80, 84 and 85 to a desired number of turns such that the potential lateral force exerted by the catheter tip 42 is maintained below a level which could shear the wire off the catheter tip.

In operation, the catheter system is introduced by an incision into the femoral artery and routed through the vascular system into the desired chamber of the patient's heart. Once the proper chamber is reached, reciprocal movement of the handle 18, together with depression and rotation of the knob 70, produces precise control of intricate vertical and lateral movement of the tip member 42 such that any point on the wall of the chamber is readily accessible to the electrodes. The electrode members 44, 46 and 48 can be utilized to map the cardiac depolarization potentials throughout the chamber, thereby locating and mapping the early activation site. The tip electrode is used to transfer the energy for tissue ablation, and is used in a mapping mode.

Of course, as shown in the FIGS. 5A-5C and 6, the catheter tip may be configured in any desired specialized shape to better address specific sites or internal cardiac areas. This may be accomplished by providing a variety of electrode catheter tip sections of predetermined fixed shapes as by using memoried materials such as metal alloys and plastics. An example of these is shown in FIGS. 5A and 5B in the form of a supra valvular mapping and ablation tip designed to address the atrial side of the A-V ring. The configuration of FIG. 5C is pre-shaped to address the ventricular side of the A-V ring. The catheter tip, generally at 100, includes a segment of one of several predisposed configurations such as those shown at 102, 104 and 106, having an approximate length of 4.2 cm (for a tip equipped with 6 4 mm ring electrodes with 3 mm spacing therebetween). A wire tail segment 108 which is about 2.0 cm in length and is included in FIGS. 5A and 5B aids in stabilizing precise placement of the electrodes. The catheter tip further contains a highly flexible proximal segment 110 which may be about 8.5 cm in length and operates to maneuver the pre-shaped portion. The electrode section includes individually connected and separately operable ring electrodes 112 separated by spaces 114. The electrodes may be of any convenient size and spacing.

FIG. 5C shows another specialized controlled shape for the tip 100 in which the side arm segment 106 is straight. This shape has been found useful in intravascular mapping and ablation at the ventricular side of the A-V ring and for accessing the posterior accessory pathways (AP) in its directed configuration and for use in addressing the left free wall AP in a right directed version. The remainder of the flexible tip section at 118 is similar to the flexible tip section 110 of FIGS. 5A and 5B and 40 of FIG. 2 being attached to the main catheter tube 120 as by a transition at 122.

The precision of the lateral displacement possible with the catheter system of the invention makes catheter-initiated ablation of tissue with respect to curing heart arrhythmias much easier and more precise. This makes the procedure less time-consuming and much more practical than with previous systems.

Figure 6:
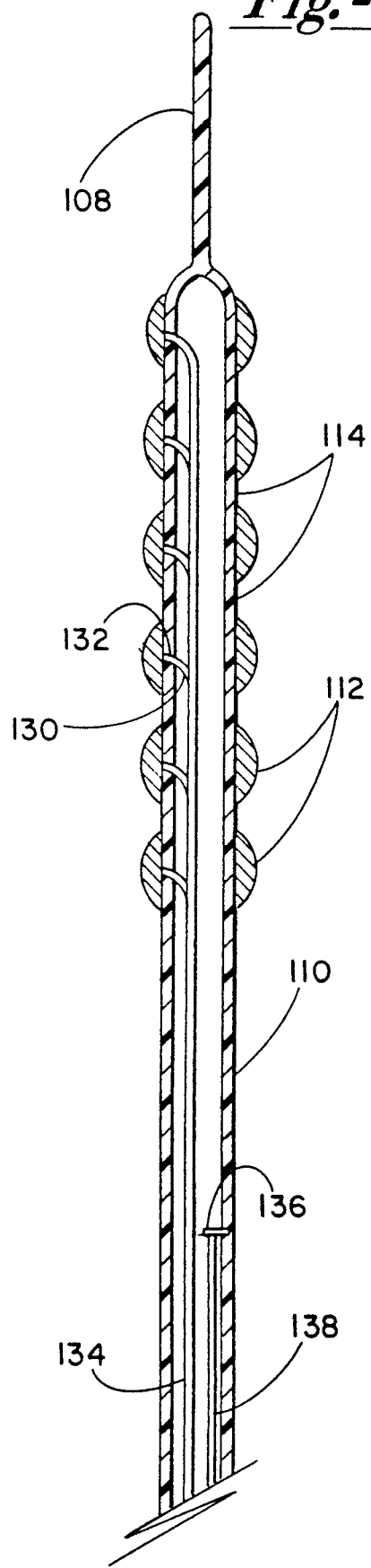
FIG. 6 represents an enlarged detailed view, partially in section, of an electrode mapping/ablation tip in accordance with FIGS. 5A-5C.

FIG. 6 details a typical electrode catheter tip with a plurality of ring electrodes 112 spaced laterally at 114. Each electrode is individually connected to an insulated conductor 130 as at 132. The conductors are bundled together as at 134 and are conveyed to controls outside the catheter in a well-known manner. A control pin 136 together with a control wire 138 are also provided for the flexible segment 110 to maneuver the devices as described above.

With respect to the deflectable catheter system of the invention, it is further contemplated, and illustrated in a further embodiment, that the pull wire used to deflect the catheter in the vertical direction be modified to also provide the lateral deflection of the catheter tip such that control can be achieved in the manner of the present invention utilizing a single control wire. In this embodiment, the pull wire is one which not only responds well to the application of tension but one which also is made out of a highly torqueable material capable of transmitting rotational force to the tip. In this manner, when the wire is subjected to tension, the tip will deflect vertically a desired amount; and when the wire is rotated, it will also transmit the rotational torque to the catheter tip and translate it into lateral deflection. A catheter control handle embodiment that achieves such control utilizing a single control wire is depicted in FIGS. 7 and 8A-8C.

FIG. 7 depicts the alternative handle system, generally at 140, which is shown broken just above the area of attachment of the distal end of the main ablation catheter system tube 142 and extending to the electrical jack or plug-in device at the proximal end of the handle at 144 having multiple input/output pick-off points as at 145. The multiple pick-off points 145 are connected to a plurality of wire members as at 146 which in turn are contained in a flexible conduit housing or tube 147 which navigates the entire catheter system to connect the tip electrodes in a well-known manner. This is typically a length of nylon tubing that protects the wires and is able to navigate the center of the catheter system so that it is easily twisted and untwisted so as to be unaffected by relative rotation and reciprocal movement of intermediate parts.

The handle 140 includes an outer housing member 148 containing a cylindrical bore 150 in which a piston member 152 is reciprocally movable. The piston 152 has an enlarged piston handle 154 which can be held by the operator with the handle such that the housing 148 can be hand rotated with respect to the piston member 152.

The multi-functional control wire is depicted at 157 and has its distal end secured through a bore or opening 155 and is wound about a rotatable retaining member 156 which is mounted between a pair of oppositely disposed bores in the handle 140 and is capable of rotation with respect to the bores as by using the slotted screw head at 158. In this manner, the tension in the control wire 157 is initially adjusted when the handle is first assembled or repaired or as adjusted and retained in place by friction; thereafter wire tension is controlled by the hand operated reciprocal motion of the piston handle 154.

The piston 152 is further provided with a segment of sets of barbs or grooves 160 and barbs or ridges 162 which are located on opposite sides of the piston 152 and which cooperate with a ring 164 and wires 166 to release and retain the piston as can be seen in greater detail with regard to FIGS. 8A-8C. A further ring 168 is provided which cooperates with ears 170 to lock the ring 164 in place and with it ring 164. A rubber O-ring or the like 172 seals the proximal shaft portion of the piston 174 and provides the desired amount of friction with respect to free reciprocal motion of the piston.

In order to limit the number of turns of the housing 148 relative to the piston handle 154, a threaded rotation limiting device is designed into the handle. The proximal portion of the cylinder carrying the piston 152, possibly 6 cm, is provided with one or more longitudinal shallow recesses or slots 176, typically 3 mm wide by 5 mm deep, for example, which allow the passage of a corresponding one or more pins 178 which extend from a nut 180 threaded on a proximal hollow screw portion or threaded shaft extension 182 of piston 152 which further carries a positive stop member 184. Rotation of the handle housing 148 relative to the piston 152/154 causes the nut member 180 to be displaced along the threaded segment 182 according to the thread pitch, rotation of the nut 180 being prevented by the pin or pin projections 178 contacting the groove(s) 176. Such displace is limited proximally by the stop member 184 and distally by the proximal piston segment 174.

The nut 180 is preferably placed at or about the midpoint of the threaded segment 182 when assembled so that available left or right rotation turns are about equal. In this manner, the relative rotation of the control wire 157 anchored to the member 158 is limited to 8–10 turns to prevent torsional fracture. Of course, relative rotation of the handles 148 and 154 causes the wire conduit 147 to twist about the wire 157. Enough slack is provided in the flexible tube 147, however, to allow for the full number of rotational turns allowed. In the longitudinal direction, tension is adjusted by movement of the piston relative to the cylinder as the wire 157 is also secured to the piston.

Control of the reciprocal motion of the piston system is best shown in FIGS. 8A–8C which illustrate a locking mechanism for the piston 152. In this regard, a pair of oppositely disposed deep grooves 186 contain spaced parallel wire 166. The spaced wire 166 engages the relevant barbs 162 to lock the piston in place when the member 152 is rotated to one position and allow free reciprocal passage of the member 152 when the member 152 is rotated 90° to a position where no ridges engage the wires.

Another alternate two-wire control handle is depicted by FIG. 9 and includes a handle housing 190 having a cylinder recess 192 receiving a reciprocally adjustable piston 194 sealed by O-ring 195 and connected to a rotating lateral deflection wire control ring 196 through which the electrical control wires 198 and longitudinal deflection wire 200 are centrally threaded into the main catheter tube 202. The electrical connector is depicted at 204. Torque is applied to a lateral deflection wire 204 mounted through a tube 206 which branches off from the main catheter tube 202 by means of an internal ring gear 208 and pinion or follower gear 210 (or transfer wheel) 210 to which the wire 204 is fixed. A single rotation of the ring gear member will produce a number, possibly up to 8, rotations of the pinion gear 210 which, in turn, imparts the multiplied rotational torque to the lateral deflection control wire 204. Reciprocal operation of the piston 192 controls the longitudinal (vertical) deflection wire tension and rotation of the ring gear 208 controls torsion on the lateral control wire 204.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:
1. A catheter comprising:
   (a) a flexible, tubular distal catheter section extending a main catheter tube and describing a distal catheter lumen and having a working distal tip area to be precisely controlled and including a distal tip;
   (b) a single multi-function manipulation control means for manipulative control of the distal tip area and having a distal end anchored at or near the distal tip of the distal catheter section and operable in a manner such that the application of controlled longitudinal tension to the multi-function manipulation control means produces a corresponding controlled longitudinal bending of the distal tip area and the controlled application of rotational torque to the multi-function deflection control means produces a corresponding controlled radial deflection of the distal tip area in a plane substantially parallel to a direction of the applied rotational torque; and
   (c) wherein the combined application of longitudinal tension and rotational torque to the control element provides three-dimensional manipulative control of the working distal tip section.

2. The apparatus of claim 1 further comprising a tail segment attached to or as a continuation of the distal tip of the distal catheter section to aid in positioning and stabilizing the distal tip area.

3. The apparatus of claim 1 wherein the manipulation control means is a tension and torque transmitting control wire, said apparatus further comprising torque control means comprising: a self-locking, hand-rotatable knob for applying controlled rotational torque to said control wire.

4. The apparatus of claim 3 wherein said manipulation control means comprises a hand-operable reciprocating piston means for applying controlled longitudinal tension to said control wire.

5. The apparatus of claim 2 wherein at least a portion of the distal catheter section is predisposed to assume a predetermined non-linear shape, such that the shape is resumed upon deployment of the distal section.

6. The apparatus of claim 5 wherein the working distal tip area of the distal catheter section further comprises a plurality of spaced electrodes suitable for both mapping and ablation.

7. The apparatus of claim 1 wherein the working distal tip area of the distal catheter section further comprises a plurality of spaced electrodes suitable for both mapping and ablation.

8. The apparatus of claim 1 wherein the manipulation control means is characterized by having greater flexibility in a portion traversing the distal catheter lumen.

9. The apparatus of claim 1 further comprising system control means for applying said longitudinal tension and rotational torque to the multi-function manipulation control means.

10. The apparatus of claim 1 wherein the manipulation control means is a control wire and wherein the manipulation control means is threaded through the distal catheter lumen.

11. The apparatus of claim 10 further comprising a main catheter tube describing a lumen and wherein the manipulation control means is threaded through the main catheter tube.

12. The apparatus of claim 1 wherein at least a portion of the distal catheter section is predisposed to assume a predetermined non-linear shape, such that the shape is resumed upon deployment of the distal catheter section.

13. The apparatus of claim 12 wherein the working distal tip area of the distal catheter section further comprises a plurality of spaced electrodes suitable for both mapping and ablation.

14. A single element manipulation control system for a catheter comprising:
   (a) a main catheter tube describing a lumen therein;
   (b) a flexible, tubular distal catheter section extending the main catheter tube, having an external surface and describing a distal catheter lumen and having a working distal tip area to be precisely controlled and including a distal tip;
   (c) electrode means for establishing electrical connection with adjacent tissue surfaces comprising at least one electrode carried by the working distal tip area in communication with the external surface of the distal catheter section;
   (d) a control system for controlling said working distal tip area comprising an independent multifunction manipulation control element threaded loosely within the main catheter tube and the distal catheter lumen and having a distal end anchored at or near the distal tip of the distal catheter section and operable in a manner such that the application of tension to the control element axially displaces the control element and produces a corresponding controlled axial deflection or bending of the distal tip and the application of rotational torque to the control element produces a corresponding controlled radial deflection of the distal tip in a plane substantially parallel to a direction of the applied rotational torque;
   (e) wherein the application of a combination of axial tension and rotational torque to the control element provides three-dimensional manipulative control of the working distal tip section; and
   (f) control means for applying said axial tension and rotational torque to the multi-function manipulation control element comprising:
      (1) a control handle means for manipulating the distal tip area containing a cylindrical recess, a reciprocal piston means for operating the control means with the control handle means disposed in and reciprocally operable in the cylindrical recess and attached to the control means such that reciprocal motion of the piston causes a corresponding axial displacement of the multi-function manipulation control element and thereby controls the axial deflection of the distal tip; and
      (2) wherein the piston means is retained in hand-rotatable relation to the handle means such that the rotation of the piston means with respect to the handle means applies said rotational torque to the multi-function manipulation control element which the control element transmits to the distal tip thereby causing the distal tip to deflect radially correspondingly as desired.

15. The apparatus of claim 14 wherein at least a portion of the distal catheter section is predisposed to assume a predetermined non-linear shape, such that the shape is resumed upon deployment of the distal section.

16. The apparatus of claim 15 further comprising a tail segment attached to or as a continuation of the distal tip of the distal catheter section to aid in positioning and stabilizing the electrode means.

17. The apparatus of claim 14 wherein the electrode means further comprises a plurality of spaced electrodes suitable for both mapping and ablation.

18. The apparatus of claim 14 further comprising means for providing and adjusting an initial longitudinal tension in the control means.

19. The apparatus of claim 14 wherein the piston means further comprises an external, hand-operable piston handle means for controlling the movement of the piston means.

20. The apparatus of claim 19 further comprising locking means for preventing the unwanted relative movement of the piston means.

21. The apparatus of claim 20 wherein the piston locking means further comprises at least one series including a plurality of longitudinally spaced, aligned retention ridges subtending a minor arc on a surface of the piston means and a laterally mounted retention means for limiting travel of the piston means fixed to the control means handle and extending across a segment of the cylindrical recess, the piston means further having a corresponding flat sector rotated from the retention ridges, cooperation being such that the piston means is freely reciprocally adjustable in the cylindrical recess when rotated so that the flat sector addresses the lateral retention means and is retained in position when rotated so that a retention ridge addresses the lateral retention means.

22. The apparatus of claim 21 further comprising a pair of oppositely disposed series of retention ridges separated by a pair of oppositely disposed flat sectors and wherein said laterally mounted retention means includes a pair of oppositely disposed laterally mounted retention means.

23. The apparatus of claim 14 further comprising relative rotation limiting means associated with and limiting the relative rotation of the handle and the piston means.

24. The apparatus of claim 23 wherein the rotating limiting means includes:
   (a) a threaded rider means for limiting travel along and adapted to ride between predetermined extremes on a threaded shaft for carrying the threaded rider means fixed to the distal end of the piston means and including rotation preventing means preventing the rider means from rotating with the threaded shaft such that rotation of the threaded shaft causes relative displacement of the threaded rider means therealong; and
   (b) stop means limiting the travel of the rider means such that relative rotation between the rider means and the threaded shaft means and so torque applied to the control means is limited in either direction.

25. The apparatus of claim 24 wherein the rotation preventing means includes at least one lateral projection means for preventing rotation and wherein the cylindrical recess is provided with one or more longitudinal grooves for receiving the projection means and in which it rides.

26. A method of mapping the electrical cardiac depolarization potentials and ablating tissue comprising the steps of:
   (a) introducing a deflectable cardiac mapping and ablation catheter system into a vascular system of a patient, the catheter system comprising:
      (1) a catheter having a flexible, tubular distal catheter section describing a distal catheter lumen and having a distal tip sought to be precisely controlled;

(2) a single element control means for axial and radial deflection control disposed and extending within the distal catheter lumen and having a distal end anchored at a point at or near the distal end of the flexible distal catheter section and operable in a manner such that the reciprocal movement of the control means deflects or bends the distal tip of the catheter in a plane substantially parallel a direction of movement of the control means and such that the application of rotational torque to the control means when the tip is bent produces a corresponding deflection of the distal tip of the catheter in a radial plane substantially parallel to the direction of the applied rotational torque;

(3) means for reciprocally displacing the single element control means along the flexible distal catheter lumen; and (4) means for applying rotational torque to the single element control means;

(5) tip electrode means comprising at least one electrode carried by an electrode segment of the distal catheter section connected through the catheter system and in communication with an external surface of the distal catheter section;

(b) adjusting the combined tension and torsion in the single element control means to deflect and steer the electrode means to access the tissue surface of the chamber as required;

(c) using the tip electrode means to detect and map cardiac depolarization potentials; and (d) operating said tip electrode means to ablate early activation sites as indicated.

27. The method of claim 26 further comprising the steps of:

(d) using a distal tip segment of the flexible tubular distal catheter section configured in a predetermined non-linear shape to more closely match the shape of a surface of a designated cardiac area; and (e) maneuvering the predetermined non-linear shape to match and map and/or ablate the tissue surface of said specifically designated cardiac area.

28. A system for controlling manipulation of a catheter tip area in three-dimensional space comprising:

(a) a catheter device having a proximal and a distal end an axis and a distal catheter tip area to be controlled at or proximate the distal end thereof;

(b) independent manipulation means associated with said catheter device, the manipulation means further comprising a control element for the controlled bending of said catheter tip area, in a plane substantially parallel to the axis thereof, responsive to the application or relaxation of axial tension, and for the controlled radial manipulation of the catheter tip area, by the application of rotational torque, such that a combined application of axial tension and rotational torque to the control element produces three-dimensional manipulative control of the catheter tip; and (c) control means associated with said manipulation means for applying or relaxing axial tension and rotational torque thereto.

29. The apparatus of claim 28 wherein the manipulation means comprises a single wire element.

30. The apparatus of claim 29 wherein the catheter device further comprises a catheter tube having a wall and describing a lumen therein and wherein said single wire element is threaded along said catheter tube and loosely contained within the catheter lumen and attached to the tube wall in the catheter tip area.

31. A dual-element catheter tip control system comprising:

(a) a catheter having a highly flexible, tubular distal catheter section having a distal end and describing a distal catheter lumen and having a distal tip sought to be precisely controlled;

(b) a first deflection control element threaded within the distal catheter lumen and having a distal end anchored at a point at or near the distal end of the flexible distal catheter section in a manner such that the axial displacement thereof deflects the distal tip of the catheter axially in a plane substantially parallel a direction of element movement;

(c) means for axially displacing the first deflection control element further comprising:

(1) a hand-operated control handle having an axially displaceable section attached to the first deflection control element, the axial motion of which causes a corresponding axial displacement of the first deflection control element and thereby controls the axial deflection of the distal tip;

(d) a second deflection control element threaded within the distal catheter lumen and having a distal end anchored at or near the distal end of the flexible distal catheter section in a manner such that the application of rotational torque to the second deflection control element produces a corresponding radial deflection of the distal tip of the catheter in a plane substantially parallel to the direction of the applied rotational torque; and (e) means for applying said rotational torque to the second deflection control element further comprising:

(1) a self-locking, hand-rotatable radial adjustment control knob mounted from the control handle and attached to the second deflection control element in a manner such that rotation of the knob left or right applies a corresponding rotational torque to the second deflection control element which transmits it to the distal tip thereby causing the distal tip to deflect radially as desired.

32. A dual-element catheter tip control system comprising:

(a) a catheter having a highly flexible, tubular distal catheter section having a distal end and describing a distal catheter lumen and having a distal tip sought to be precisely controlled;

(b) a first deflection control element threaded within the distal catheter lumen and having a distal end anchored at a point at or near the distal end of the flexible distal catheter section in a manner such that the movement of the first deflection control element axially along in the distal catheter lumen deflects the distal tip of the catheter in a plane substantially parallel a direction of element movement;

(c) means for axially displacing the first deflection control element along the flexible distal catheter lumen comprising:

(1) a hand-operated control handle having a longitudinally displaceable section attached to the first deflection control element, the longitudinal motion of which causes a corresponding longitudinal displacement of the first deflection control element and thereby controls the axial deflection of the distal tip;

(d) a second deflection control element threaded within the distal catheter lumen and having a distal end anchored at or near the distal end of the flexible distal catheter section in a manner such that the application of rotational torque to the second deflection control element produces a corresponding radial deflection of the distal tip of the catheter in a plane substantially parallel to the direction of the applied rotational torque; and (e) means for applying said rotational torque to the second deflection control element further comprising:

(1) a rotatable ring gear means associated with an internal pinion gear connected to the second deflection control wire in a manner such that rotation of the ring gear causes a corresponding opposite rotation of the pinion gear, rotation of the pinion gear applying a corresponding amount of rotational torque to the second deflection control element which, in turn, transmits the torque to the distal tip and translating the torque into control to cause the distal tip to deflect radially as desired.

* * * * *

UNITED STATES PATENT AND TRADEMARK OFFICE
CERTIFICATE OF CORRECTION

PATENT NO. : 5 327 905
DATED : July 12, 1994
INVENTOR(S) : Boaz Avitall

It is certified that error appears in the above-indentified patent and that said Letters Patent is hereby corrected as shown below:

In column 10, line 32, delete ":".

In column 13, line 20, delete "and".

In column 13, line 22, after ";", insert -- and -- .

In column 13, line 38, delete "(d)", and insert -- (e) -- .

In column 13, line 42, delete "(e)", and insert -- (f) -- .

In column 13, line 48, after "end", insert -- , -- .

Signed and Sealed this

Twenty-third Day of January, 1996

Attest:

BRUCE LEHMAN

*Attesting Officer*       *Commissioner of Patents and Trademarks*